(12) United States Patent
Fukutomi

(10) Patent No.: US 6,186,984 B1
(45) Date of Patent: Feb. 13, 2001

(54) CANNULA GUIDE DEVICE

(75) Inventor: Osamu Fukutomi, Gifu (JP)

(73) Assignee: Fukutomi Healthscience and Services Company, Gifu (JP)

( * ) Notice: Under 35 U.S.C. 154(b), the term of this patent shall be extended for 0 days.

(21) Appl. No.: 09/314,151

(22) Filed: May 19, 1999

(30) Foreign Application Priority Data

Oct. 27, 1998 (JP) .................................................. 10-305157

(51) Int. Cl.$^7$ .................................................. A61M 5/178
(52) U.S. Cl. .................. 604/165.01; 604/164.01
(58) Field of Search ..................... 604/164, 165, 604/263, 162, 164.01, 164.07, 165.01, 165.02, 165.04, 164.03

(56) References Cited

U.S. PATENT DOCUMENTS

| | | | |
|---|---|---|---|
| 4,966,586 | * 10/1990 | Vaillancourt | 604/164 |
| 5,250,036 | * 10/1993 | Farivar | 604/164 |
| 5,542,930 | * 8/1996 | Schur | 604/164 |
| 5,681,288 | * 10/1997 | Schlitt | 604/164 |
| 5,913,845 | * 6/1999 | Brimhall | 604/165 |

* cited by examiner

*Primary Examiner*—John G. Weiss
*Assistant Examiner*—Cris I. Rodriguez
(74) *Attorney, Agent, or Firm*—Dorsey & Whitney LLP

(57) ABSTRACT

A cannula guide device that can provide a secure and safe transfusion treatment is disclosed, comprising a cannula assembly and a needle assembly. The cannula assembly includes a cannula and a cannula holder, and the needle assembly includes a guide needle and a needle holder. The cannula guide device is characterized in that a rotary cannula arrangement is provided to steadily send the cannula relative to the guide needle toward a patient without generating a repulsive force on the needle holder to avoid pulling out the guide needle accidentally.

6 Claims, 4 Drawing Sheets

(a)

(b)

(c)

(a)

(b)

(c)

(a)

(b)

(c)

CANNULA GUIDE DEVICE

BACKGROUND OF THE INVENTION

1. Field of the Invention

This invention relates generally to a cannula guide device. More particularly, this invention relates to a cannula guide device that can securely and safely guide a cannula into a blood vessel or tract of a patient without accidental removal of its already pricked guide needle from the patient's blood vessel or tract, or without undue damage to the patient's blood vessel or tract or skin by the guide needle, or without undue pains to the patient.

2. Prior Art

It is generally time consuming to perform blood transfusion or fluid transfusion on a patient. Before, a patient was required to undergo a long and often painful fluid transfusion treatment with a conventional injection needle to be inserted into his or her blood vessel or tract. The patient had to stay substantially motionless during the long transfusion treatment in order to prevent the injection needle from accidentally coming off his or her blood vessel or tract. If the injection needle accidentally comes off, the injection needle must be pricked into the patient again. The patient's awkward movement might additionally cause damage onto his or her blood vessel or tract or even skin with the sharp needle end, which would inevitably accompany considerable pains to be suffered by the patient.

Cannula guide devices have been introduced in replacement of such conventional injection needle devices so as to perform safer and securer and thus less painful fluid transfusion on a patient who needs transfusion treatment, to a great benefit not only to the patient but also to the medical personnel who performs the transfusion treatment upon the patent.

A conventional cannula guide device is comprised of a needle holder, a cannula and a guide needle axially secured to the needle holder. The guide needle is provided through the fluid passage of the cannula with its forward or distal end protruding a few millimeters from the distal end of the cannula so as to be pricked ahead of the cannula into a patient's blood vessel or tract hypodermically. The cannula is then pushed or pulled and slid forward or distally on the axially provided internal guide needle into the blood vessel or tract. When the distal end of the cannula is pricked or inserted into the blood vessel or tract, the guide needle is pulled rearward or proximally and removed from the blood vessel or tract and eventually from the cannula entirely in order to clear the fluid passage of the cannula for transfusion treatment. Blood or fluid is then pumped into or extracted from the blood vessel or tract through the fluid passage of the cannula.

Such a conventional cannula guide device provides an invaluable benefit to patients who need transfusion treatment as well as medical personnel who perform transfusion on such patients, but not without a serious shortcoming. The shortcoming that inevitably accompanies conventional cannula guide devices is described hereinunder using the accompanying FIG. 5 (prior art), in which a cannula guide device 80 is shown comprising a cannula 61, a guide needle 71, a cannula base 70b, and a needle holder 70a. The guide needle 71 is provided through the fluid passage (not shown) formed through the cannula 61. The rear or proximal end of the cannula 61 is secured to the forward or distal end of the cannula base 70b.

After the guide needle 71 is pricked into a blood vessel or tract 90 of a patient (not shown) a couple of millimeters deep, the cannula guide device 80 is generally held with four fingers as shown in FIG. 5. The cannula base 70b is held between a thumb and index finger of one hand, while the needle holder 70a is held between the other thumb and index finger. The cannula 61 is pushed (or pulled) forward or distally in the direction shown by an arrow F1 to be inserted into the blood vessel or tract 90 where the guide needle 71 has been pricked, while the needle holder 70a is carefully held still. Otherwise, the needle holder 70a may be inadvertently pulled rearward or proximally in the direction shown by an arrow F2 as a reaction, which would pull the pricked guide needle 71 inadvertently out of the blood vessel or tract 90, and may cause damage on the blood vessel or tract 90 or the patient's skin. Such can likely happen when the medical performer is pressed for time. The guide needle 71 must be pricked into the blood vessel or tract 90 over again, to the physical as well as mental detriment of the patient, which would be equally detrimental to the medical performer.

SUMMARY OF THE INVENTION

Accordingly, it is an object of the present invention to provide an improved cannula guide device that can safely and securely insert its cannula into a patient's blood vessel or tract without generating awkward reactive force on its needle holder and guide needle.

The above object of the invention can be achieved by providing a rotary cannula arrangement that can rotate and advance its cannula on the axially provided guide needle instead of pushing or pulling the cannula.

Such a rotary cannula arrangement is provided such that the cannula holder is rotated with a finger or fingers of one hand coaxially with the needle holder in a prearranged direction relative to the needle holder so as to gradually and steadily advance the cannula on the guide needle into a patient's blood vessel or tract, while the needle holder is held substantially motionless with the other hand. There will hardly be caused "reactive motion" on the needle holder for the cannula is not pushed or pulled forward or distally. Accordingly, accidental detachment of the guide needle from the patient's blood vessel or tract can be effectively avoided.

The foregoing feature of the invention may be provided by providing the distal end of the needle holder with a slant surface and the proximal end of the cannula holder with a protrusion to be turned and slid along the slant surface forward, while adequately preventing accidental detachment of the needle holder and the cannula holder from each other. With this arrangement, the cannula holder and cannula can advance forward relative to the needle holder and the guide needle without "kicking back" the needle holder when the cannula holder is coaxially rotated by means of the protrusion relative to the needle holder, as will be described hereinafter in more detail referring to the accompanying drawings.

Such a feature of the invention may alternatively be provided by providing a thread mating arrangement between the needle holder and the cannula holder, as will be described in detail hereinafter using the accompanying drawings. The cannula whose proximal end is coaxially secured to the distal end of the cannula holder gradually and steadily advances on the guide needle as the cannula holder advances, without generating reactive force on the needle holder.

BRIEF DESCRIPTION OF THE DRAWINGS

FIG. 1(b) shows the cannula guide device of FIG. 1(a), where the cannula and cannula holder are dismantled;

FIG. 1(c) shows the dismantled cannula and cannula holder;

DESCRIPTION OF PREFERRED EMBODIMENT

Figure 1:
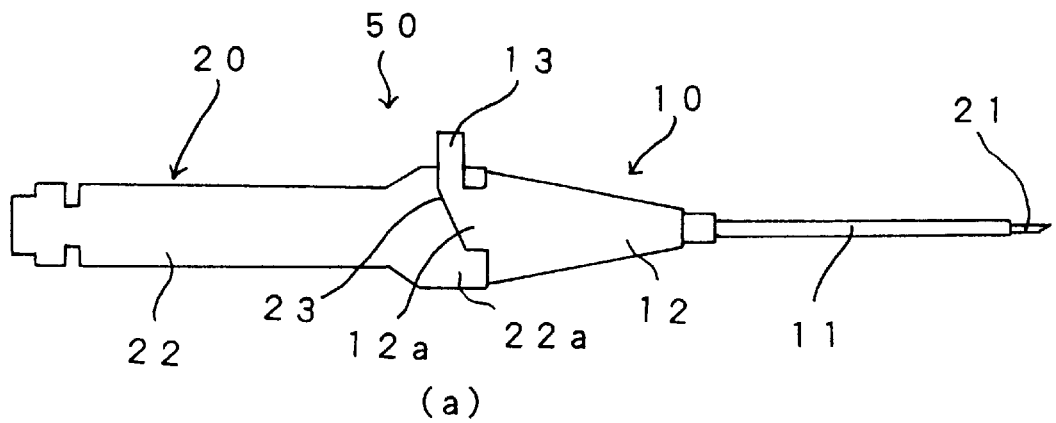
FIG. 1(*a*) shows a cannula guide device according to an embodiment of the present invention.
Figure 1:
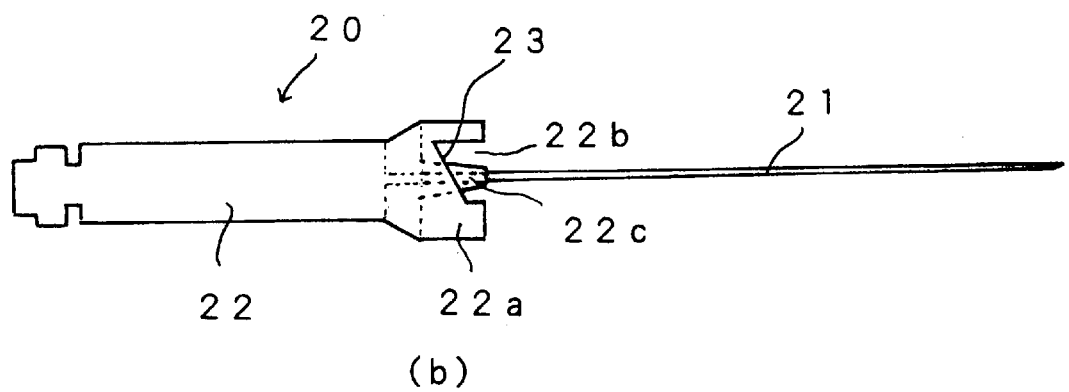
Figure 1:
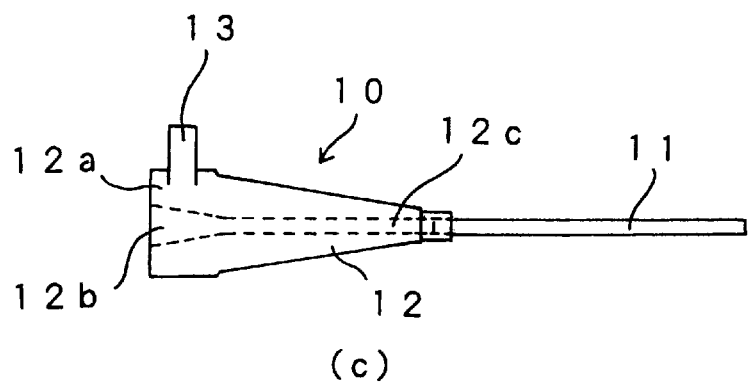
Figure 2:
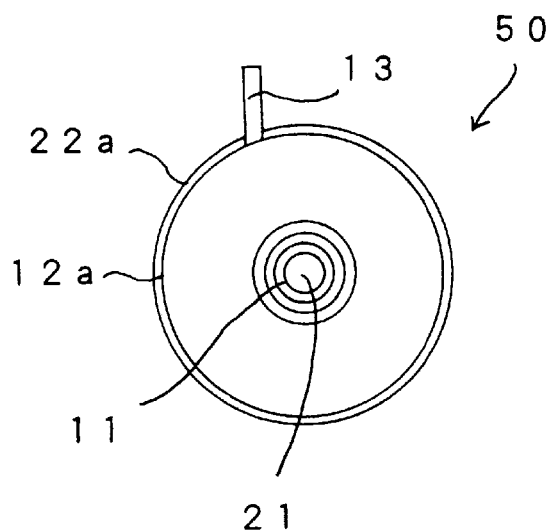
FIG. 2 is an enlarged front view of the cannula guide device.
Figure 3:
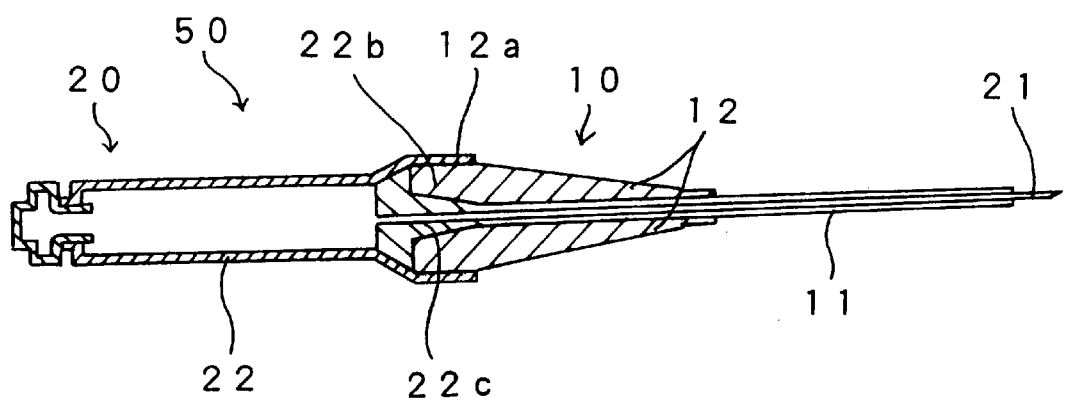
FIG. 3 is a longitudinal sectional view of the cannula guide device.

In FIG. 1 is shown a cannula guide device 50 according to an embodiment of the present invention. The cannula guide device 50 is comprised of a needle assembly 20 and a cannula assembly 10. The needle assembly 20 is comprised of a guide needle 21 and a generally cylindrical needle holder 22 having a conical needle base 22c on its distal end. The cannula assembly 10 is comprised of a cannula 11 and a generally conical cannula holder 12 having a conically formed opening which faces rearward. The cannula holder 12 is provided with a plate-like protrusion 13 on its outer surface as shown in FIG. 2. The protrusion 13 may take any suitable configuration as long as it provides a "protrusion" large enough to sufficiently catch a finger and slide on the slant surface 23 (to be described) without slipping off. The guide needle 21 is coaxially secured on the conical needle base 22c.

The needle holder 22 is additionally provided with a receptacle 22b enclosed with a circumferential wall 22a whose diameter is considerably larger than that of the cylindrical portion of the needle holder 22. The receptacle 22b houses the conical needle base 22c and receives the proximal end of the conical cannula holder 12 to be capped on the conical needle base 22c, the conical opening 12b accommodating the needle base 22c. The receptacle 22b is provided on its distal portion with a slant surface 23 in order to provide the cannula holder 12 with a gradual forward movement when the protrusion 13 is hooked and turned with a finger of a transfusion performer and slid on the slant surface 23 forward as can be readily appreciated by a person skilled in the relevant art.

The conical cannula holder 12 is provided with an axial fluid passage 12c in fluid communication with the cannula 11, which is widened and conically shaped near its proximal opening to provide the aforementioned conically formed opening such that the widened passage portion can properly mate with and securely seat itself on the conical needle base 22c as described earlier.

The cannula guide device 50 of the present invention is utilized as follows. The guide needle 21 is inserted through the cannula holder 12 and the cannula 11 from the proximal end of the cannula holder 12 till the distal end of the guide needle 21 protrudes a few millimeters from the distal end of the cannula 11. The cannula holder 12 is mounted on the needle base 22c as described earlier such that the protrusion 13 is seated at the proximal end of the slant surface 23. The exposed distal end or tip of the guide needle 21 is pricked into a blood vessel or tract of a patient (not shown) through the skin of the patient by sending the needle holder 22 forward carefully relative to the cannula holder 12 and cannula 11 which are to be held stationary.

Next, the distal end of the cannula 11 is guided into the blood vessel or tract of the patient utilizing the above-described feature of the present invention. When the cannula holder 12 is turned with a finger of one hand utilizing the protrusion 13 toward the distal end of the slant surface, the protrusion 13 slides along the slant surface 23 toward the distal end of the slant surface 23, gradually sending the cannula holder 12 and the cannula 11 forward. The needle holder 22 is simply held stationary with the other hand. There is no need to reactively pull the needle holder 22 proximally. Therefore, accidental removal of the guide needle 21 from the blood vessel or tract is adequately prevented until the cannula 11 is properly seated in the blood vessel or tract.

The guide needle 21 of the cannula guide device 50 is generally made of stainless steel, and the cannula 11 is generally made of soft resin material such as polyethylene. The needle holder 22 and the cannula holder 12 are generally made of rigid resin material such as polyurethane or polypropylene. However, as will be appreciated by a person skilled in the relevant art, any appropriate materials can be utilized to provide the foregoing members. Advantageously, a smoothing agent such as stearic acid is added to the cannula holder and/or the needle holder materials to decrease the friction or promote the sliding property between them.

Figure 4:
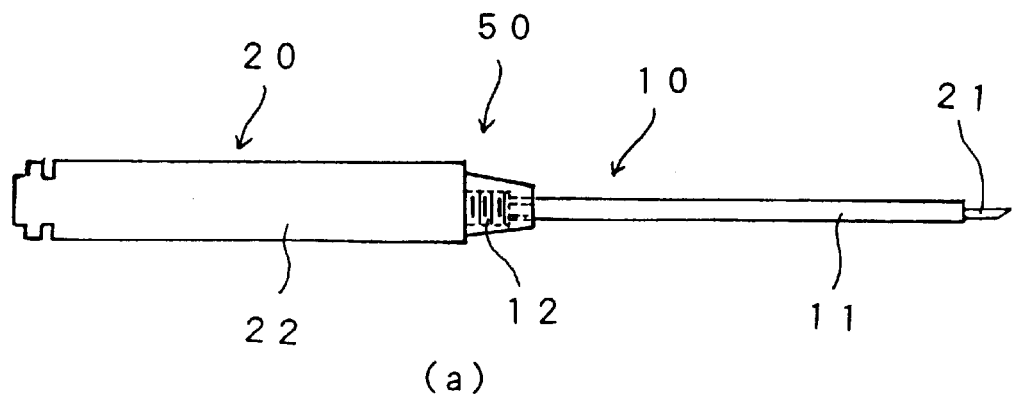
FIG. 4(a) shows an alternative cannula guide device according to another embodiment of the present invention.
FIG. 4(b) shows the cannula guide device of FIG. 4(a), where the cannula and cannula holder are removed.
FIG. 4(c) shows the removed cannula and cannula holder.
Figure 4:
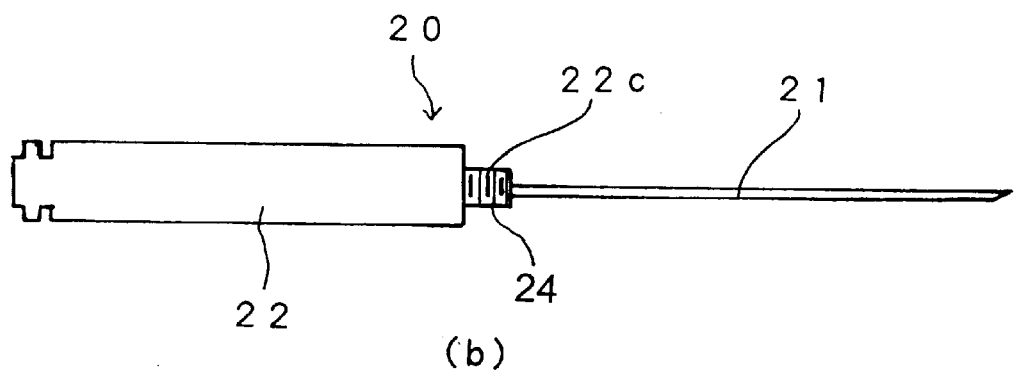
Figure 4:
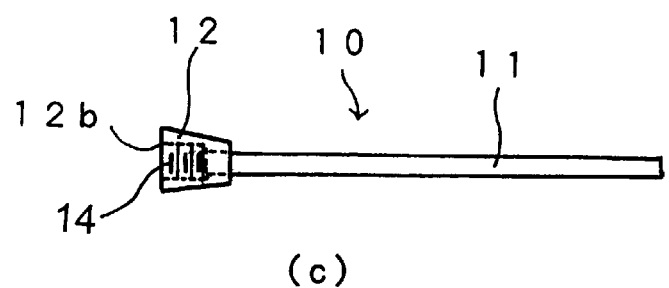
Figure 5:
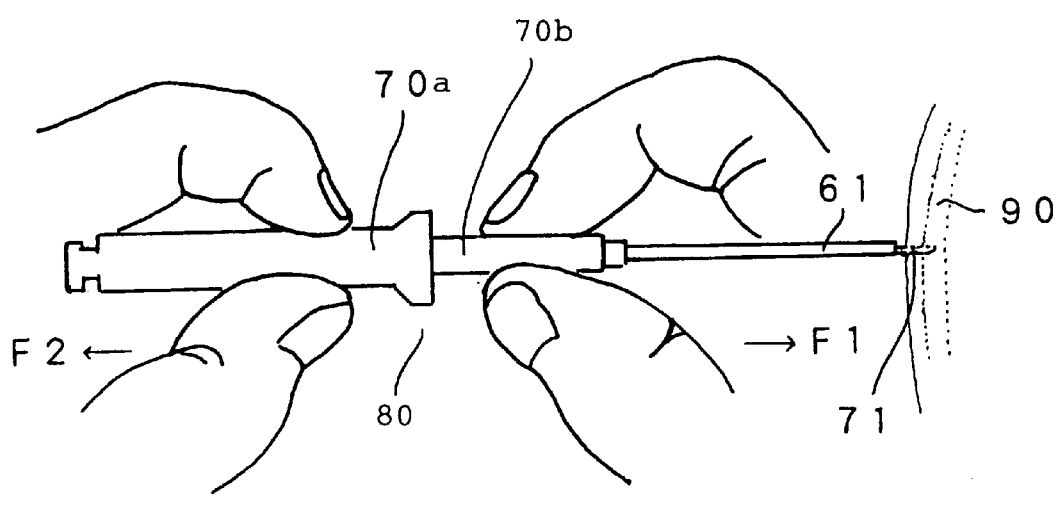
FIG. 5 shows a conventional cannula guide device and an example use.

FIG. 4 shows an alternative cannula guide device 50 of the present invention. This cannula guide device 50 is comprised of a needle assembly 20 and a cannula assembly 10 as the foregoing embodiment. The needle assembly 20 is comprised of a guide needle 21 and a generally cylindrical needle holder 22. The cylindrical needle holder 22 is provided on its distal end with a needle base 22c where the proximal end of the guide needle 21 is secured. The needle base 22c is provided with a thread 24 on its outer surface. The cannula assembly 10 is comprised of a cannula 11 and a cannula holder 12 which has a threaded receptacle 14 that can mate with the thread 24 of the needle base 22c.

The use of this cannula guide device 50 is practically identical with that of the previously introduced cannula guide device except that the cannula holder 12 of this embodiment engages the needle base 22c in a "bolt-nut" manner. As will be easily appreciated, the cannula holder 12 and the cannula 11 are gradually and steadily sent forward relative to the guide needle 21 into a blood vessel or tract of a patient as they are turned with fingers of a medical performer in the thread loosening direction, while the needle holder 22 is held stationary. It is not required to reactively pull the needle holder 22 proximally. The tip of the guide needle 21 can safely and steadily stay in the blood vessel or tract of the patient while the cannula 21 is being sent into the blood vessel or tract of the patient.

It is to be appreciated that the foregoing embodiments are only for illustration of the present invention. Accordingly, modifications or changes can be made to the invention without departing from the teachings of the present invention. The scope of the invention is only to be limited as necessitated by the accompanying claims.

What is claimed is:

1. A cannula guide device comprising:

(a) a cannula assembly having a conical shape, wherein the cannula assembly comprises a cannula and a cannula holder;

(b) a needle assembly, wherein the needle assembly comprises a guide needle and a needle holder;

(c) a protrusion connected to the cannula holder; and (d) a needle base having a conical shape connected to the guide needle, (e) wherein the needle holder comprises a receptacle, wherein the receptacle includes:
  (1) the needle base and the proximal end of the cannula holder, and
  (2) a slant surface, wherein the slant surface provides the cannula holder with a forward movement when the protrusion is hooked and turned.

2. The cannula guide device of claim 1 further comprising a rotary cannula arrangement, wherein the cannula arrangement can rotate the cannula assembly relative to the needle assembly and steadily send the cannula assembly distally or toward a patient.

3. The cannula guide device of claim 1, wherein the needle holder is cylindrical.

4. The cannula guide device of claim 3 wherein the receptacle is enclosed with a wall whose diameter is larger than the cylindrical portion of the needle holder.

5. The cannula guide device of claim 1 wherein the cannula holder includes an fluid passage in fluid communication with the cannula.

6. The cannula guide device of claim 1, wherein tip of the guide needle is pricked in a blood vessel of patient by sending the needle holder forward relative to the cannula holder and cannula which are held stationary.

\* \* \* \* \*